(12) United States Patent
Kwon et al.

(10) Patent No.: US 8,268,292 B2
(45) Date of Patent: Sep. 18, 2012

(54) OBOVATOL HAVING ANTI-ANXIETY ACTIVITY

(75) Inventors: Byoung Mog Kwon, Daejeon (KR); Seung Ho Lee, Chungcheongbuk-do (KR); Kwang Hee Son, Daejeon (KR); Jin Tae Hong, Chungcheongbuk-do (KR); Ki Wan Oh, Chungchoengbuk-do (KR); Jeong Ju Seo, Chungcheongbuk-do (KR)

(73) Assignees: Korea Research Institute of Bioscience and Biotechnology, Daejeon (KR); Chungbuk National University Industry-Academic Cooperation Foundation, Chungcheongbuk-do (KR)

( * ) Notice: Subject to any disclaimer, the term of this patent is extended or adjusted under 35 U.S.C. 154(b) by 707 days.

(21) Appl. No.: 11/913,734

(22) PCT Filed: May 4, 2006

(86) PCT No.: PCT/KR2006/001687
§ 371 (c)(1), (2), (4) Date: Nov. 6, 2007

(87) PCT Pub. No.: WO2006/121258
PCT Pub. Date: Nov. 16, 2006

(65) Prior Publication Data
US 2008/0194702 A1    Aug. 14, 2008

(30) Foreign Application Priority Data
May 6, 2005 (KR) .................. 10-2005-0037854

(51) Int. Cl.
*A61K 9/68* (2006.01)
*A61K 31/075* (2006.01)
*A01N 31/14* (2006.01)
(52) U.S. Cl. .......................................... 424/48; 514/719
(58) Field of Classification Search .................. 424/48; 514/719
See application file for complete search history.

(56) References Cited

U.S. PATENT DOCUMENTS
5,135,746 A * 8/1992 Matsuno et al. .............. 424/725

FOREIGN PATENT DOCUMENTS
JP          10338631      * 12/1998

OTHER PUBLICATIONS
Pyo et. al. (Arch. Pharm. Res. (2002) 25:325-328).*

* cited by examiner

*Primary Examiner* — Marcos Sznaidman
(74) *Attorney, Agent, or Firm* — Lucas & Mercanti, LLP

(57) ABSTRACT

The present invention relates to obovatol compound isolated from *Magnolia obovata* Thunb. for the prevention and treatment of anxiety disorders involved with CNS. The obovatol compound isolated from *Magnolia obovata* Thunb. have potent anti-anxiety activity, verified by an increased percentage of time on the open arms, an increased number of entries into, time spent on, the distal portion of the open arms, and a decreased activity of locomotor. Therefore it can be used as the therapeutics or health care food for treating and preventing anxiety disorders.

6 Claims, 5 Drawing Sheets

OBOVATOL HAVING ANTI-ANXIETY ACTIVITY

CROSS-REFERENCE TO RELATED APPLICATION

This patent application claims the benefit of priority from Korean Patent Application No. 10-2005-0037854, filed on May 6, 2005, through PCT Application Serial No. PCT/KR2006/001687 filed on May 4, 2006, the contents of which are incorporated herein by reference.

TECHNICAL FIELD

The present invention related to a composition comprising obovatol showing potent anti-anxiety activity and the use thereof.

BACKGROUND ART

Anxiety is a fundamental emotion and a normal response in some warm-blood animals including human, which is characterized by an apprehensive uneasiness of mind usually associated with an impending or anticipated experience that may be problematic. When such apprehension becomes disproportionate and overwhelming, it is termed an anxiety neurosis which can be characterized by helplessness, tension, uneasiness, faintness or even panic syndrome. This anxiety status can also be accompanied by physiological signs such as heart palpitation, gasping, sweating, dry mouth and nausea. The mechanism by which anxiety is induced in the Central Nervous System (CNS) is complex (Haefely W., Psychopharmacology of Anxiety, *Eur. Neuropsychopharmacol.*, Vol. 1, pp. 89-95, 1991).

Anxiety and depressive disorders are the most common psychiatric diseases. Both are known to be associated with major impairment and adverse consequences in later life. Estimates of the prevalence of any childhood anxiety disorder are in the order of 3 to 12% and rise to as high as 40% or over and most of impairment is not required for a diagnosis. In general, epidemiological studies show that rates of any anxiety disorders are higher in children than adolescents. In contrast, rates of depressive disorder in young people show higher rates in adolescence than in childhood. Depression and anxiety in childhood and adolescence have long-term deleterious outcomes for a significant proportion of young people. Depression and anxiety, once experienced in childhood are very likely to recur in adulthood. Early onset of depressive and anxiety are also associated with substantial social impairment. Even sub-clinical levels of depression in children and adolescents are associated with significant morbidity in the form of psychosocial impairment and service utilization. Furthermore, adolescents identified as having high levels of depressive or anxiety symptoms are significantly more likely to experience depressive disorder in adulthood than adolescents with depression levels within the normal range. The observations that sub-clinical symptoms of depression are associated with significant morbidity rate and those high level of depression and anxiety symptoms predict depressive and anxiety disorders together with the evidence that depression and anxiety can be regarded as continua (Costello E J et al., The Great Smoky Mountains Study of Youth, Goals, design, methods, and the prevalence of DSM-III-R disorders, *Arch Gen Psychiatry*, 53, pp. 1129-1136, 1996).

Specifically, anxiety symptoms or disorders frequently precede depressive symptoms or disorders. Moreover although certain sub-types of anxiety, namely social phobia and panic rarely precede depression, individuals with those disorders and depression are very likely to have had a different anxiety disorder that predated the onset of depression.

Anxiety disorders are the most common diseases among psychiatric illnesses. It is severed to leave the patient dysfunctional. In addition to the subjective feeling of anxiety and panic, physiological changes such as tachycardia, palpitations, sweating and trembling are reported. Secondary insomnia is commonly observed in patients with anxiety, with complaints of difficulty in getting to sleep and of frequent walking from sleep. Symptoms of anxiety often accompany withdrawal from sedatives, or may arise from the use of stimulants such as amphetamines. It is reported that lactate infusion and hyperventilation produce subjective symptoms and objective signs of anxiety, and are associated with decreased vagal tone, i.e., decreased parasympathetic activity (George et al., *Arch. Gen. Psych.*, 46, pp. 153-156, 1989).

There remain several requirements as an ideal anti-anxiety medicine such that it should not cause sleepiness and should keep patient calm without physical and spiritual problems.

At present, benzodiazepine, diazepam, oxazepam, prazepam, lorazepam, alprazolam, helazepam and clonazepam are extensively used as representative anti-anxiety drugs, most of which induce sedation and sleepy syndrome (YOON D. J., A side effect of psychiatric drug, *Journal of Korean Medical Association*, 38(10), pp. 1196-1202, 1995). It has been reported that benzodiazepine, most frequently used anti-depressant drug in spite of their side-effects such as sedation, muscle-relaxation, amnesia, and dependence etc, increases the affinity for GABA receptor, a major inhibitory transmitter in the CNS (Central Nervous System) to induce the influx of $Cl^-$ ions into the cells. The development of new anti-anxiety agent without other side effects such as addition, withdrawal syndrome, and so on has been still needed till now. (Mary J. et al., *Pharmacology $2^{nd}$ edition*, Lipincott Williams & Wilkins, pp. 89-93, 2000).

*Magnolia obovata* has been traditionally used as stomachics and the leave thereof has been reported to be edible in Asian countries such as Korea and Japan. There has been also reported that the plant contains various ingredients such as β-eudesmol, β-pinene, magnolil and honokiol (Chung B. S. and Shin M. K., *HyangyakDaesacheon*, Youngrimsa, pp. 469-471, 1998).

However, there have been no disclosure or suggestion that obovatol isolated from the extract of *Magnolia obovata* shows anti-anxiety activity in any of above cited literatures, the disclosures of which are incorporated herein by reference incorporated herein.

DISCLOSURE OF INVENTION

Technical Problem

Accordingly, there have been studied and investigated to develop new satisfactory anti-anxiety agents which can solve the problem of conventional drugs, in particular, which can improve anti-anxiety efficacy and provide with safe long-term administration without adverse action till now.

Present inventors extensively investigated to find effective drug showing potent anti-depressant activity from natural resource, particularly *Magnolia obovata* and finally, obovatol isolated therefrom shows more potent anti-anxiety activity comparing with commercially used diazepam without side effect such as drowsiness.

Technical Solution

The present invention provides a pharmaceutical composition comprising obovatol and the pharmacologically acceptable salt thereof as an active ingredient in an effective amount to treat and prevent anxietydisorder involved with CNS.

The present invention also provides a use of obovatol and the pharmacologically acceptable salt thereof showing strong anti-anxiety activity.

The present invention also provides a method of treating or preventing anxiety in a mammal comprising administering to said mammal an effective amount of obovatol, together with a pharmaceutically acceptable carrier thereof.

Thus, the present invention provides a pharmaceutical composition comprising obovatol represented by following chemical formula (I), or a pharmaceutically acceptable salt thereof as an active ingredient in an effective amount to treat and prevent anxietydisorder involved with CNS.

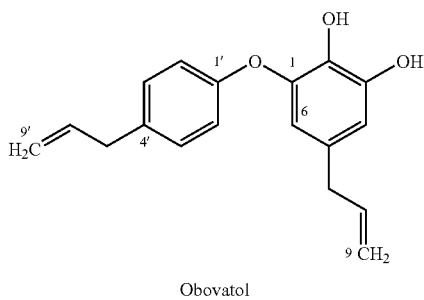

Obovatol

The present invention provides a pharmaceutical composition comprising obovatol represented by Chemical formula (I), or a pharmaceutically acceptable salt thereof as an active ingredient.

The obovatol of the present invention can be isolated from *Magnolia obovata* Thunb. or synthesized by general procedure well known in the art.

The inventive compound represented by general formula (I) can be transformed into their pharmaceutically acceptable salt and solvates by the conventional method well known in the art. For the salts, acid-addition salt thereof formed by a pharmaceutically acceptable free acid thereof is useful and can be prepared by the conventional method. For example, after dissolving the compound in the excess amount of acid solution, the salts are precipitated by the water-miscible organic solvent such as methanol, ethanol, acetone or acetonitrile to prepare acid addition salt thereof and further the mixture of equivalent amount of compound and diluted acid with water or alcohol such as glycol monomethylether, can be heated and subsequently dried by evaporation or filtrated under reduced pressure to obtain dried salt form thereof.

As a free acid of above-described method, organic acid or inorganic acid can be used. For example, organic acid such as methansulfonic acid, p-toluensulfonic acid, acetic acid, trifluoroacetic acid, citric acid, maleic acid, succinic acid, oxalic acid, benzoic acid, lactic acid, glycolic acid, gluconic acid, galacturonic acid, glutamic acid, glutaric acid, glucuronic acid, aspartic acid, ascorbic acid, carbonylic acid, vanillic acid, hydroiodic acid and the like, and inorganic acid such as hydrochloric acid, phosphoric acid, sulfuric acid, nitric acid, tartaric acid and the like can be used herein.

Further, the pharmaceutically acceptable metal salt form of inventive compounds may be prepared by using base. The alkali metal or alkali-earth metal salt thereof can be prepared by the conventional method, for example, after dissolving the compound in the excess amount of alkali metal hydroxide or alkali-earth metal hydroxide solution, the insoluble salts are filtered and remaining filtrate is subjected to evaporation and drying to obtain the metal salt thereof. As a metal salt of the present invention, sodium, potassium or calcium salt are pharmaceutically suitable and the corresponding silver salt can be prepared by reacting alkali metal salt or alkali-earth metal salt with suitable silver salt such as silver nitrate.

The pharmaceutically acceptable salt of the present compound comprise all the acidic or basic salt which may be present at the compounds, if it does not indicated specifically herein. For example, the pharmaceutically acceptable salt of the present invention comprise the salt of hydroxyl group such as the sodium, calcium and potassium salt thereof; the salt of amino group such as the hydrogen bromide salt, sulfuric acid salt, hydrogen sulfuric acid salt, phosphate salt, hydrogen phosphate salt, dihydrophosphate salt, acetate salt, succinate salt, citrate salt, tartarate salt, lactate salt, mandelate salt, methanesulfonate(mesylate) salt and p-toluenesulfonate (tosylate) salt etc, which can be prepared by the conventional method well known in the art.

The inventive compound isolated *Magnolia obovata* Thunb. of the present invention may be prepared in accordance with the following preferred embodiment.

Hereinafter, the present invention is described in detail.

For the present invention, for example, the dried leave of *Magnolia obovata* Thunb is cut into small pieces and the piece was mixed with 2 to 20-fold, preferably, 5 to 10-fold volume of non-polar solvent such as hexane, chloroform, ethylacetate, acetone, or the mixtures thereof, preferably chloroform; and was heated at the temperature ranging from 20 to 100° C., preferably from 20 to 50° C., for the period ranging 1 to 48 hours, preferably 15 to 30 hours, by reflux extraction with hot water, cold water extraction, ultra-sonication or conventional extraction, preferably by cold water extraction; the residue was filtered and then the filtrate is dried to obtain non-polar solvent soluble extract thereof.

The non-polar solvent soluble extract prepared by the above step is further fractioned with ethylacetate to collect ethylacetate-soluble layer. The ethylacetate-soluble layer was cooled, concentrated with vaccuo to obtain the concentrates. The concentrates were dissolved in methanol and subjected to C18 column chromatography using mixed solvent (methanol:water=4:1). The active component dissolved in methylene chloride was further subjected to silica gel column chromatography (Daisogel IR-60-W-40:63 mm) filled with silicagel eluting with mixture solvent of hexane: chloroform with changing the mixed ratio (9:1 to 6:4) to obtain more purified active component. The purified component was then purified by HPLC eluting with mixture solvent of methanol: water (4:1) to obtain final obovatol compound showing potent anti-anxiety activity.

Also, above described procedures may be modified or subjected to further step to fractionate or isolate more potent fractions or compounds by conventional procedure well-known in the art, for example, the procedure disclosed in the literature (Harborne J. B. Phytochemical methods: *A guide to modern techniques of plant analysis*, 3$^{rd}$ Ed. pp 6-7, 1998).

The compound of the present invention prepared from the above-described method shows potent anti-anxiety activity and therefore, it may be employed to treat or prevent anxiety disorder involved with CNS.

It is an object of the present invention to provide a use of obovatol isolated from *Magnolia obovata* Thunbor pharmaceutically acceptable salts thereof for the preparation of therapeutic agent for treatment and prevention of anxiety.

The term "anxiety disorder involved with CNS" disclosed herein comprises such as panic disorder, obsessive-compulsive disorder, stress disorder, society morbid fear, and generalized anxiety disorder.

In accordance with another aspect of the present invention, there is also provided a use of the obovatol compound for manufacture of medicines employed for treating or preventing anxiety disorder involved with CNS such as panic disorder, obsessive-compulsive disorder, stress disorder, society morbid fear, and generalized anxiety disorder.

In accordance with another aspect of the present invention, there is also provided an method of treating or preventing anxiety related to central nervous system such as panic disorder, obsessive-compulsive disorder, stress disorder, society morbid fear, and generalized anxiety disorder, wherein the method comprises administering a therapeutically effective amount of the obovatol or pharmaceutically acceptable salts thereof.

The compound according to the present invention can be provided as a pharmaceutical composition containing pharmaceutically acceptable carriers, adjuvants or diluents. For example, the compound of the present invention can be dissolved in oils, propylene glycol or other solvents which are commonly used to produce an injection. Suitable examples of the carriers include physiological saline, polyethylene glycol, ethanol, vegetable oils, isopropyl myristate, etc., but are not limited to them. For topical administration, the compound of the present invention can be formulated in the form of ointments and creams.

The compound of the present invention has potent anti-anxiety activity, and the pharmaceutical composition of the present invention thus may be employed to treat or prevent anxiety disorders.

Hereinafter, the following formulation methods and excipients are merely exemplary and in no way limit the invention.

The compound of the present invention in pharmaceutical dosage forms may be used in the form of their pharmaceutically acceptable salts, and also may be used alone or in appropriate association, as well as in combination with other pharmaceutically active compounds.

The compound of the present invention may be formulated into preparations for injections by dissolving, suspending, or emulsifying them in aqueous solvents such as normal saline, 5% Dextrose, or non-aqueous solvent such as vegetable oil, synthetic aliphatic acid glycerides, esters of higher aliphatic acids or propylene glycol. The formulation may include conventional additives such as solubilizers, isotonic agents, suspending agents, emulsifying agents, stabilizers and preservatives.

The desirable dose of the inventive compound varies depending on the condition and the weight of the subject, severity, drug form, route and period of administration, and may be chosen by those skilled in the art. However, in order to obtain desirable effects, it is generally recommended to administer at the amount ranging 0.0001-100 mg/kg, preferably 0.001 10 mg/kg by weight/day of the inventive compound of the present invention. The dose may be administered in single or divided into several times per day. In terms of composition, the compound should be present between 0.0001 to 10% by weight, preferably 0.0001 to 1% by weight based on the total weight of the composition.

The pharmaceutical composition of present invention can be administered to a subject animal such as mammals (rat, mouse, domestic animals or human) via various routes. All modes of administration are contemplated, for example, administration can be made by inhaled, orally, rectally or by intravenous, intramuscular, subcutaneous, intrathecal, epidural or intracerebroventricular injection.

The compound of the present invention also can be used as a main component or additive and aiding agent in the preparation of various functional health food and health care food.

The term "functional health food" defined herein the functional food having enhanced functionality such as physical functionality or physiological functionality by adding the compound of the present invention to conventional food to prevent or alleviate anxiety disorders in human or mammal.

It is the other object of the present invention to provide a health care food comprising the obovatol compound isolated from *Magnolia obovata* Thunb. together with a sitologically acceptable additive for the prevention and alleviation of anxiety disorders.

The term "health care food" defined herein the food containing the compound of the present invention showing no specific intended effect but general intended effect in a small amount of quantity as a form of additive or in a whole amount of quantity as a form of capsule, pill, tablet etc.

The term "sitologically acceptable additive" defined herein "any substance the intended use which results or may reasonably be expected to result-directly or indirectly-in its becoming a component or otherwise affecting the characteristics of any food" for example, thickening agent, maturing agent, bleaching agent, sequesterants, humectant, anticaking agent, clarifying agents, curing agent, emulsifier, stabilizer, thickner, bases and acid, foaming agents, nutrients, coloring agent, flavoring agent, sweetner, preservative agent, antioxidant, etc, which shall be explained in detail as follows.

If a substance is added to a food for a specific purpose in that food, it is referred to as a direct additive and indirect food additives are those that become part of the food in trace amounts due to its packaging, storage or other handling.

Above described health care foods can be contained in food, health beverage, dietary therapy etc, and may be used as a form of powder, granule, tablet, chewing tablet, capsule, beverage etc for preventing or improving anxiety disorders.

Also, above described compound can be added to food or beverage for prevention and improvement of anxiety. The amount of above described compound in food or beverage as a functional health food or health care food may generally range from about 0.01 to 15 w/w % of total weight of food for functional health food composition. In particular, although the preferable amount of the compound of the present invention in the functional health food, health care food or special nutrient food may be varied in accordance to the intended purpose of each food, it is preferably used in general to use as a additive in the amount of the compound of the present invention ranging from about 0.01 to 5% in food such as noodles and the like, from 40 to 100% in health care food on the ratio of 100% of the food composition.

Providing that the health beverage composition of present invention contains above described compound as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as tauma-tin, stevia extract such as levaudioside A, glycyrrhizin et al., and synthetic deodorant such as saccharin, aspartam et al., may be useful favorably. The amount of above described natural carbohydrate is generally ranges from about 1 to 20 g, preferably 5 to 12 g in the ratio of 100 mL of present beverage composition.

The other components than aforementioned composition are various nutrients, a vitamin, a mineral or an electrolyte, synthetic flavoring agent, a coloring agent and improving agent in case of cheese, chocolate et al., pectic acid and the salt thereof, alginic acid and the salt thereof, organic acid, protective colloidal adhesive, pH controlling agent, stabilizer, a preservative, glycerin, alcohol, carbonizing agent used in carbonate beverage et al. The other component than aforementioned ones may be fruit juice for preparing natural fruit juice, fruit juice beverage and vegetable beverage, wherein the component can be used independently or in combination. The ratio of the components is not so important but is generally range from about 0 to 20 w/w % per 100 w/w % present composition. Examples of addable food comprising aforementioned compound therein are various food, beverage, gum, vitamin complex, health improving food and the like.

The present invention is more specifically explained by the following examples. However, it should be understood that the present invention is not limited to these examples in any manner.

ADVANTAGEOUS EFFECTS

Present inventors extensively investigated to find effective drug showing potent anti-depressant activity from natural resource, particularly *Magnolia obovata* and finally, obovatol isolated therefrom shows more potent anti-anxiety activity comparing with commercially used diazepam without side effect such as drowsiness.

BEST MODE FOR CARRYING OUT THE INVENTION

Figure 1:
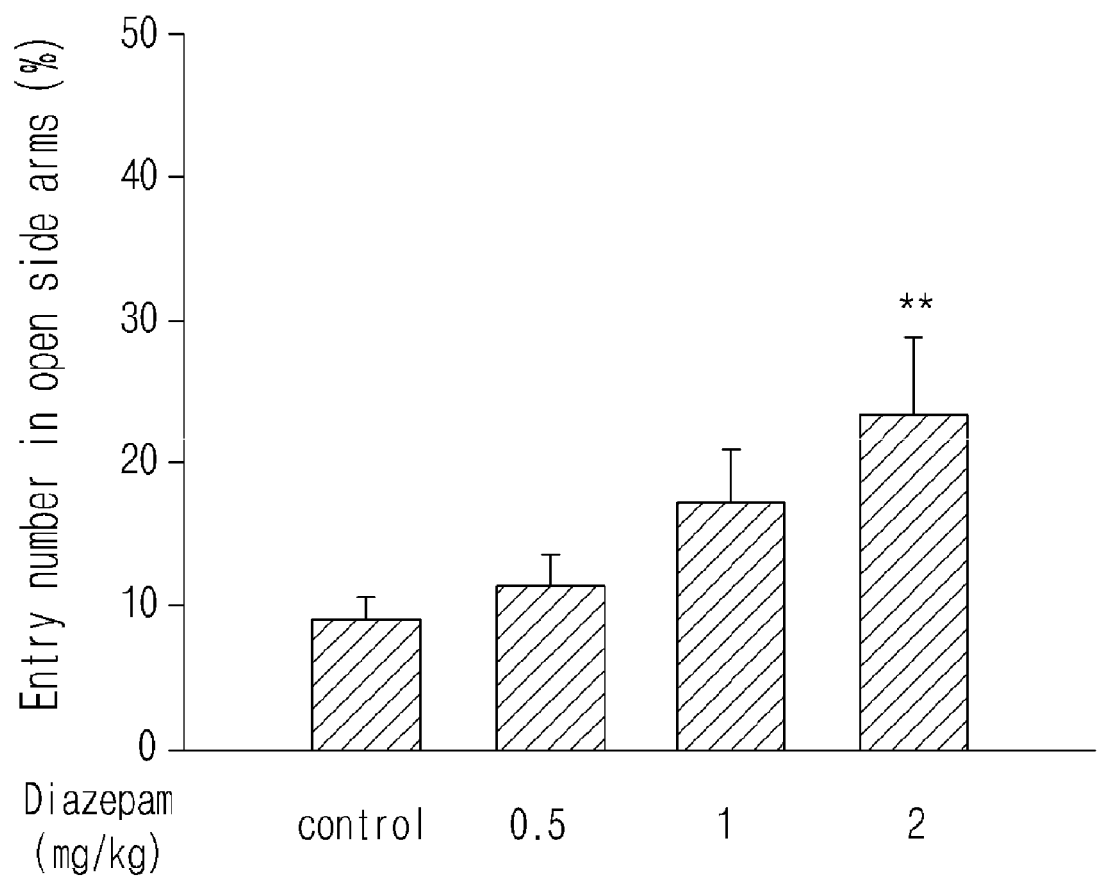
FIG. 1 shows the effect of diazepam on the number of open arm entries in elevated plus-maze model test (*$p<0.05$, $p<0.01$ and *$p<0.005$ denotes the significance comparing with positive control)

The present invention is more specifically explained by the following examples. However, it should be understood that the present invention is not limited to these examples in any manner.

Mode for the Invention

EXAMPLES

The following Examples and Experimental Examples are intended to further illustrate the present invention without limiting its scope.

Example 1

Preparation of Ovobatol from the Extract of *Magnolia obovata* Thunb 1-1. Preparation of Non-Polar Solvent Soluble Extract of *Magnolia obovata* Thunb 3 kg of dried leaves of *Magnolia obovata* Thunb harvested from Hongwon-ri, Poseung-myeon, Pyeongtaek-si, Gyeonggi-do, Republic of Korea, was sliced, mixed with 20 L of mixed solution of chloroform and acetone (1:1) and subjected to reflux extraction on water bath at 25° C. for 24 hours to obtain their filtrate. The filtrates were cooled and concentrated to obtain 200 g of non-polar solvent soluble extract of *Magnolia obovata* Thunb.

1-2. Preparation of Obovatol from Non-Polar Solvent Soluble Extract of *Magnolia obovata* Thunb The non-polar solvent soluble extract prepared from the above described Example 1-1 was fractioned with water layer and ethylacetate layer. 1 L of the water layer was extracted with ethylacetate three times to collect ethylacetate-soluble layer. The ethylacetate-soluble layer was cooled, concentrated with vaccuo to obtain 180 g of the concentrates. 180 g of the concentrates were dissolved in 500 mL of methanol and subjected to C18 column chromatography using by 1 L of mixed solvent (methanol:water=4:1) to obtain 100 g of yellowish brown colored active components from the extract. The active component dissolved in methylene chloride was further subjected to silica gel column chromatography (Daisogel IR-60-W-40:63 mm) filled with silicagel (Merck Co. No. 9385) eluting with mixture solvent of hexane: chloroform with changing the mixed ratio (9:1 to 6:4) two times to obtain more purified active component. The purified component was then purified by HPLC (Phenomex Co.; Ultracarb 10 ODS, 250×21.2 mm) eluting with mixture solvent of methanol: water (4:1) to obtain 1 g of obovatol showing following physicochemical property.

Molecular Formula: $C_{18}H_{18}O_3$;

Mass: $M^+=282$;

$^1$H-NMR (400 MHz, $CDCl_3$) ppm: 6.28(H-4, d, J=1.8 Hz), 6.56 (H-6, d, J=1.8 Hz), 3.18 (H-7, d, J=6.6 Hz), 5.97 (H-8 and H-8', m), 5.09 (H-9 and H-9', m), 6.93 (H-2' and H-6', d, J=4.3 Hz), 7.14 (H-3' and 5', d, J=4.3 Hz), 3.36 (H-7', d, J=6.6 Hz);

$^{13}$C-NMR (100 MHz, $CDCl_3$) ppm: 143 (C-1), 132.93 (C-2), 144.77 (C-3), 110.68 (C-4), 132.47 (C-5), 11.17 (C-6), 39.60 (C-7), 137.33 (C-8), 115.85(C-9), 154.98 (C-1'), 117.84 (C-2' and 6'), 129.82 (C-3' and 5'), 135.18 (C-4'), 39.38 (C-7'), 137.18 (C-8'), 115.75 (C-9').

Experimental Example 1

Anti-Depressive Activity of Obovatiol in Elevated Plus-Maze Test

To determine anti-anxiety activity of obovatol prepared in Example 1, following experiment was performed.

1-1. Preparation of Experiment

Animals and Drugs: ICR male mice weighing from 20 g to 28 g (5 or 6 weeks) were purchased from Daehan Biolink Co., Ltd. (Korea) and housed for at least 7 days prior to the experiment under 12-h light/dark cycle (lights on at 7:00 am) in a temperature-controlled (22±2° C.) animal facility. Food and water were freely accessible. All mice were maintained in accordance with the National Institute of Toxicological Research on the Korea Food and Drug Administration guideline for the care and use of laboratory animals. Diazepam (ample type) was purchased from Dea-Won Pharmaceutical Co. (South Korea) and was orally administered 30 min prior to the experiment. Obovatol was kindly gifted from Korea Research Institute of Bioscience and Biotechnology and was orally administered 60 min prior to the experiment.

Treatment of Test Sample: obovatol prepared from Example 1 was dissolved in 0.1 ml of ethanol and diluted with 0.1% Tween-80 in order to administrate with an amount of 0.1 ml/10 g per weight of test animal. Various concentrations of test sample (obovatol), i.e., 0.2, 0.5 and 1 mg/kg were orally administered at 1 hour prior to the experiment and 2 ng/kg of diazepam was peritoneally administered into animal at 30 mins prior to the experiment.

Statistics: experimental result was expressed as mean deviation and the significance of activity was evaluated in accordance with variation analysis using by ANOVA test (p0.05, p0.01 and p0.005 shows by comparing with positive control).

1-2. Determination of Anti-Anxiety Activity Using by Elevated Plus-Maze Model

To determine the anti-anxiety activity after administration of obovatol, elevated plus-maze model test was performed as follow in accordance with procedure cited in the literature (Dawson, G. R. et al., *Trends in Pharmacological Sciences*, 16, pp. 33-36, 1995).

Elevated plus-maze apparatus consists of two perpendicular open (30×5 cm) and two closed arms (30×5 cm) with 15 cm high walls, extending from the central platform (5×5 cm). The maze was elevated to a high of 38 cm above the floor level, as has been validated and described. From preliminary experiments, we found that maximum effects of diazepam were observed when diazepam was administered orally 30 min prior and obovatol 60 min prior to plus-maze placement, respectively. A standard 5-min test was employed for each mouse. All experimental sessions were recorded with a video camera mounted vertically above the maze. The activity on the open arm was evaluated as: 1) time spent on the open arms relative to the total time spent in the plus-maze, expressed as a percentage (100× time spent on open arm/total time in the plus-maze); 2) the number of entries into both open and closed arms, expressed as a percentage (100× open/total entries). Above experiment was tested under the condition of calm and fewer lighting (50 lux) between p.m. 1:30 and p.m. 4:30.

Figure 2:
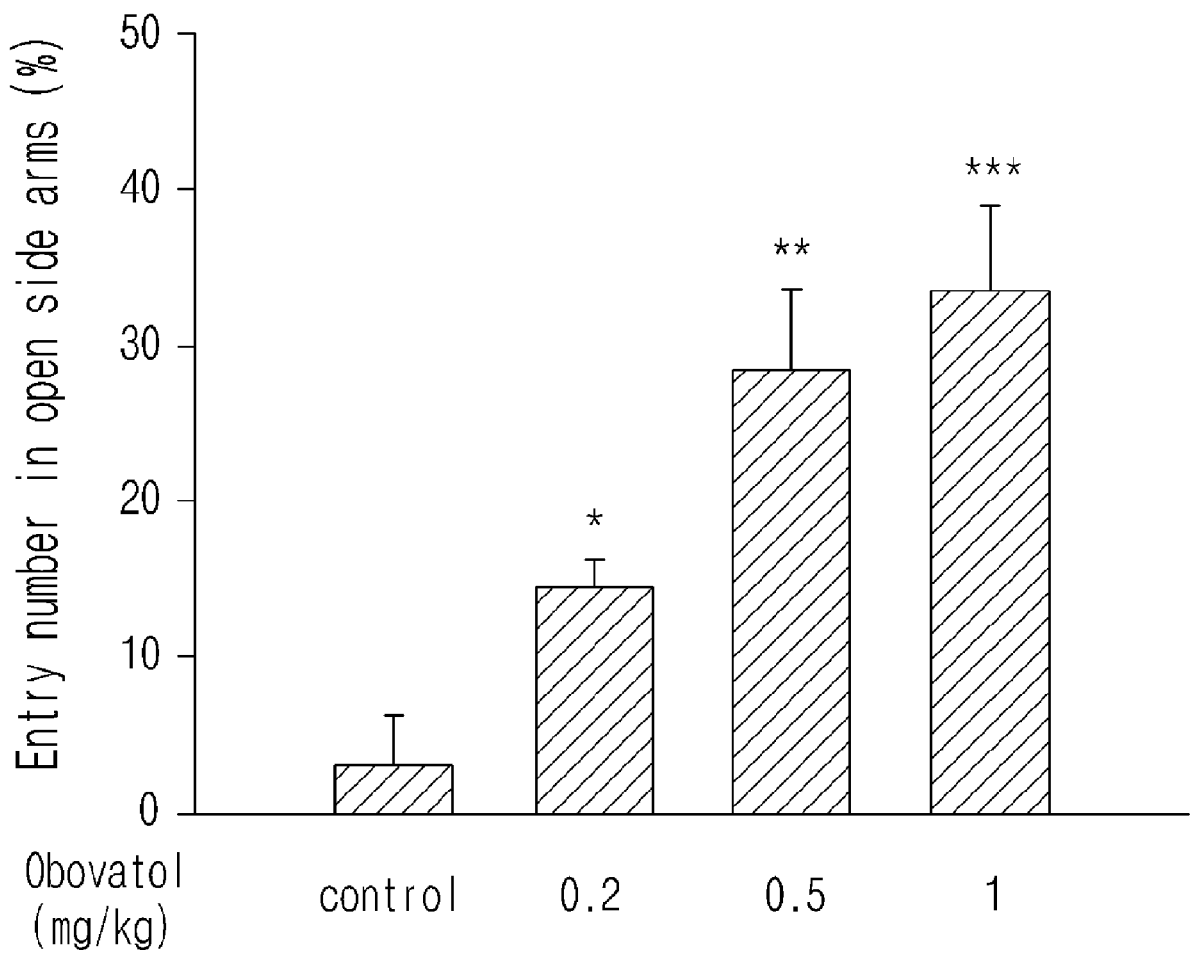
FIG. 2 shows the effect of obovatol on the number of open arm entries in elevated plus-maze model test (*$p<0.05$, $p<0.01$ and *$p<0.005$ denotes the significance comparing with positive control)

At the result of anti-anxiety test, the anti-anxiety effects after the oral administration of obovatol (0.2, 0.5, and 1.0 mg/kg) significantly increased the percentage of entries into open arms in a dose dependent manner compared with that of diazepam treated group ($P<0.05$, $P<0.05$ and $P<0.005$) (See FIG. 1 and FIG. 2). In addition, there showed significant increases in obovatol treated group at the percentage of time spent in the open arms ($P<0.05$, $P<0.05$ and $P<0.005$).

Figure 3:
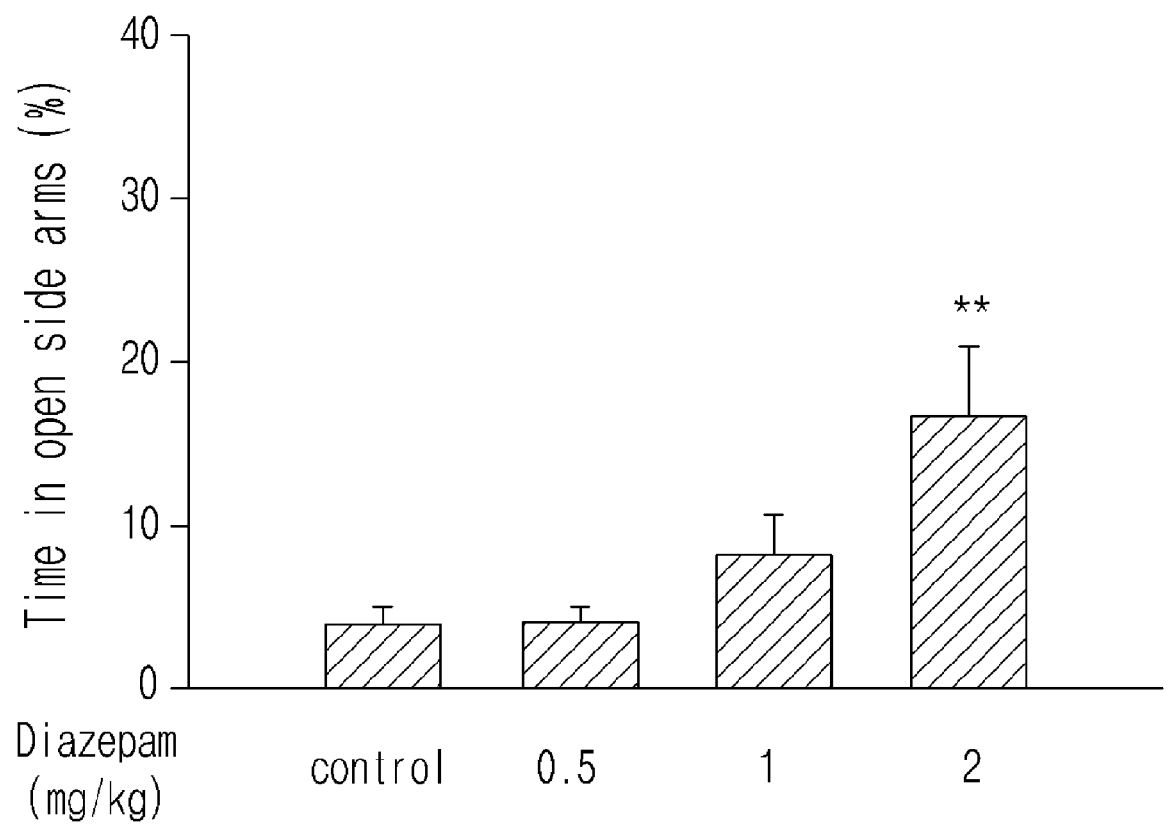
FIG. 3 represents the effect of diazepam on the spent time in open arm entries using by elevated plus-maze model test (*$p<0.05$, $p<0.01$ and *$p<0.005$ denotes the significance comparing with positive control)
Figure 4:
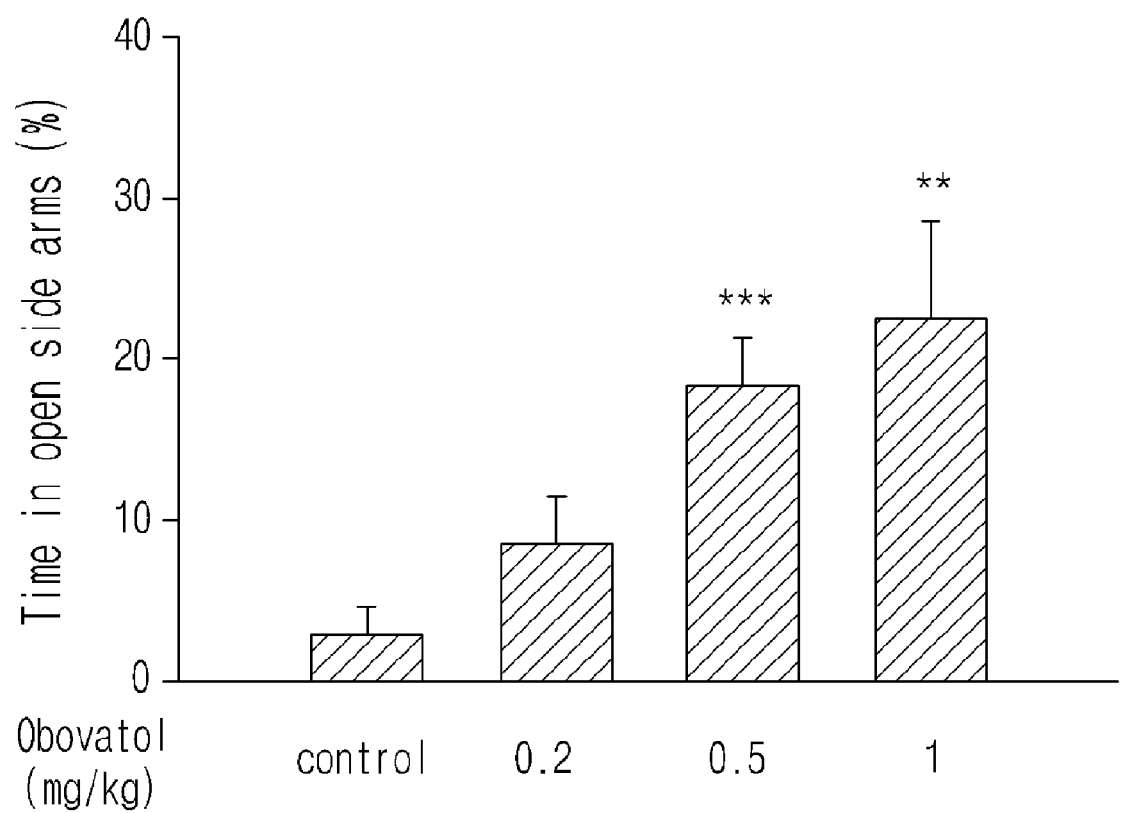
FIG. 4 represents the effect of obovatol on the spent time in open arm entries using by elevated plus-maze model test (*$p<0.05$, $p<0.01$ and *$p<0.005$ denotes the significance comparing with positive control)
Figure 5:
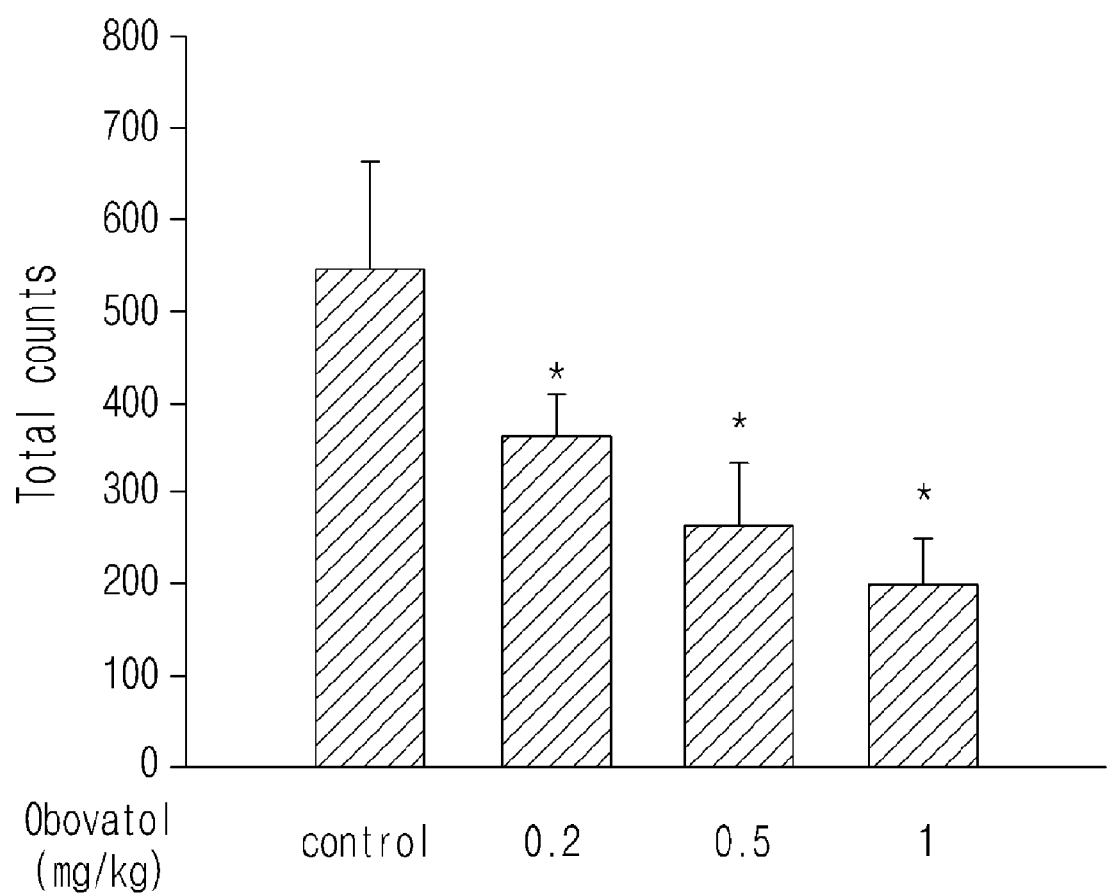
FIG. 5 presents the effect of obovatol in locomoter activity model test (*$p<0.05$, $p<0.01$ and *$p<0.005$ denotes the significance comparing with positive control).

It is confirmed that obovatol showed more potent anti-anxiety activity than diazepam at the same doses of the drugs (See FIG. 3 and FIG. 4).

Experimental Example 2

Measurement of Locomoter Activity

To determine the anti-anxiety activity of obovatol prepared by Examples 1, following experiment was performed.

2-1. Preparation of Experimental Animal

All the animals used in the test are prepared in the similar method according to Experimental Example 1.

2-2. Determination of Locomoter Activity

To determine and re-confirm the anti-anxiety activity of obovatol, following locomoter activity test was performed as follow in accordance with the procedure cited in the literature (Kulkarni S. K. et al., *Methods and Findings in Experimental and Clinical Pharmacology*, 18, pp. 219-230, 1996).

All the animals were transferred to test cage (diameter: 20 cm, height: 18 cm) one hour prior to the administration of test samples, acclimated the environment for 10 mins and the locomoter activity was determined automatically at every 1 hour.

At the result, the oral administration of various concentrations of obovatol (0.2, 0.5 and 1.0 mg/kg) significantly decreased the locomoter activity in a dose dependent manner.

Experimental Example 3

Toxicity Test

Methods

The acute toxicity tests on ICR mice (mean body weight 25±5 g) and Sprague-Dawley rats (235±10 g, Biogenomics Co., Ltd.) were performed using the obovatol compound. Four groups consisting of 3 mice or rats was administrated orally with 10 mg/kg, 100 mg/kg and 1000 mg/kg of test sample or solvents (0.2 mL, i.p.) respectively and observed for 2 weeks.

Results

There were no treatment-related effects on mortality, clinical signs, body weight changes and gross findings in any group or either gender. These results suggested that the compound prepared in the present invention were potent and safe.

Hereinafter, the formulating methods and kinds of excipients will be described, but the present invention is not limited to them. The representative preparation examples were described as follows.

Preparation of Powder

Obovatol 50 mg

Lactose 100 mg

Talc 10 mg

Powder preparation was prepared by mixing above components and filling sealed package.

Preparation of Tablet

Obovatol 50 mg

Corn Starch 100 mg

Lactose 100 mg

Magnesium Stearate 2 mg

Tablet preparation was prepared by mixing above components and entabletting.

Preparation of Capsule

Dried powder of Example 1 50 mg

Corn starch 100 mg

Lactose 100 mg

Magnesium Stearate 2 mg

Tablet preparation was prepared by mixing above components and filling gelatin capsule by conventional gelatin preparation method.

Preparation of Injection
Obovatol 50 mg
Distilled water for injection optimum amount
PH controller optimum amount Injection preparation was prepared by dissolving active component, controlling pH to about 7.5 and then filling all the components in 2 mL ample and sterilizing by conventional injection preparation method.

Preparation of Liquid
Obovatol 0.1~80 g
Sugar 5~10 g
Citric acid 0.05~0.3%
Caramel 0.005~0.02%
Vitamin C 0.1~1%
Distilled water 79~94%
$CO_2$ gas 0.5~0.82%

Liquid preparation was prepared by dissolving active component, filling all the components and sterilizing by conventional liquid preparation method.

Preparation of Health Care Food
Obovatol 1000 mg
Vitamin mixture optimum amount
Vitamin A acetate 70 mg
Vitamin E 1.0 mg
Vitamin $B_1$ 0.13 mg
Vitamin $B_2$ 0.15 mg
Vitamin B6 0.5 mg
Vitamin B12 0.2 mg
Vitamin C 10 mg
Biotin 10 mg
Amide nicotinic acid 1.7 mg
Folic acid 50 mg
Calcium pantothenic acid 0.5 mg
Mineral mixture optimum amount
Ferrous sulfate 1.75 mg
Zinc oxide 0.82 mg
Magnesium carbonate 25.3 mg
Monopotassium phosphate 15 mg
Dicalcium phosphate 55 mg
Potassium citrate 90 mg
Calcium carbonate 100 mg
Magnesium chloride 24.8 mg The above-mentioned vitamin and mineral mixture may be varied in many ways. Such variations are not to be regarded as a departure from the spirit and scope of the present invention.

Preparation of Health Beverage
Obovatol 1000 mg
Citric acid 1000 mg
Oligosaccharide 100 g
Apricot concentration 2 g
Taurine 1 g
Distilled water 900 mL Health beverage preparation was prepared by dissolving active component, mixing, stirred at 85° C. for 1 hour, filtered and then filling all the components in 1000 mL ample and sterilizing by conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

Industrial Applicability

As described in the present invention, the obovatol compound isolated from *Magnolia obovata* Thunb. shows potent anti-anxiety activity. Therefore, it can be used as the therapeutics or health care food for treating and preventing anxiety disorders caused by abnormal conditions related to central nervous system.

The invention claimed is:

1. A method for treating an anxiety disorder involved with CNS in a mammal consisting of administrating a therapeutically effective amount of obovatol or pharmaceutically acceptable salt thereof, together with a pharmaceutically acceptable carrier to a mammal.

2. The method according to claim 1, wherein the anxiety disorders are selected from the group consisting of panic disorder, obsessive-compulsive disorder, stress disorder, society morbid fear and generalized anxiety disorder in the mammal.

3. The method of claim 1, wherein the mammal is human.

4. The method of claim 2, wherein the mammal is human.

5. The method of claim 1, wherein the therapeutically amount of obovatol or pharmaceutically acceptable salt thereof is 0.001-100 mg/kg by weight/day.

6. The method of claim 5, wherein the therapeutically amount of obovatol or pharmaceutically acceptable salt thereof is 0.01-10 mg/kg by weight/day.

* * * * *